United States Patent [19]
Cauwet-Martin et al.

[11] Patent Number: 5,830,481
[45] Date of Patent: Nov. 3, 1998

[54] COSMETIC COMPOSITIONS CONTAINING A LIPID CERAMIDE COMPOUND AND A PEPTIDE HAVING A FATTY CHAIN, AND THEIR USES

[75] Inventors: Daniele Cauwet-Martin, Paris; Claude Dubief, Le Chesnay, both of France

[73] Assignee: L'Oreal, Paris, France

[21] Appl. No.: 535,671

[22] Filed: Sep. 28, 1995

[30] Foreign Application Priority Data

Sep. 29, 1994 [FR] France .................................... 94 11666

[51] Int. Cl.$^6$ ............................... A61K 7/48; A61K 7/08
[52] U.S. Cl. .................. 424/401; 424/70.1; 424/70.14; 514/844; 514/845; 514/846; 514/847
[58] Field of Search ................... 424/401, 70.1, 424/70.14; 514/844–847

[56] References Cited

U.S. PATENT DOCUMENTS

| 4,751,219 | 6/1988 | Kempen ..................................... 514/26 |
| 5,368,857 | 11/1994 | Corcoran et al. ........................ 424/401 |
| 5,476,671 | 12/1995 | Cho et al. ................................ 424/401 |

FOREIGN PATENT DOCUMENTS

| 0 278 505 | 8/1988 | European Pat. Off. . |
| 4326958 | 2/1995 | Germany . |
| WO 91/01719 | 2/1991 | WIPO . |
| WO 92/05764 | 4/1992 | WIPO . |
| WO 92/21321 | 12/1992 | WIPO . |
| 9302656 | 2/1993 | WIPO . |
| WO 93/02656 | 2/1993 | WIPO . |
| WO 94/07844 | 4/1994 | WIPO . |

OTHER PUBLICATIONS

JP 5/000923 (Abstract).
FR 2673 179 (Abstract).
DE 42244 415 (Abstract).
DE 4326958 (Abstract).

*Primary Examiner*—Jyothsna Venkat
*Attorney, Agent, or Firm*—Finnegan, Henderson, Farabow, Garrett & Dunner, L.L.P.

[57] ABSTRACT

The invention relates to new cosmetic compositions comprising, in an aqueous medium, at least one lipid ceramide compound and at least one peptide having at least one fatty chain. The invention also relates to an aqueous dispersion comprising a peptide having at least one fatty chain and at least one lipid ceramide compound.

19 Claims, No Drawings

COSMETIC COMPOSITIONS CONTAINING A LIPID CERAMIDE COMPOUND AND A PEPTIDE HAVING A FATTY CHAIN, AND THEIR USES

The present invention relates to new cosmetic compositions comprising, in an aqueous medium, at least one lipid compound of the ceramide type and at least one peptide containing at least one fatty chain.

It is well known that hair which has been sensitized (i.e., damaged and/or weakened) to various degrees through the action of environmental agents or through the action of mechanical or chemical treatments, such as dyeing, bleaching and/or permanent-waving, is often difficult to disentangle and to style, and lacks softness. In effect, through the action of these harmful factors (environmental agents, mechanical or chemical treatments), the hair loses some of its constituents, such as, in particular, ceramides and proteins.

Ceramides or their analogues are known to protect and/or repair the skin and/or the hair fibers from the harmful effects of the various agents and treatments mentioned above. In particular, they have a barrier effect which limits the leakage of proteins; they also strengthen cuticular cohesion.

In view of the fact that the protection and/or care provided by ceramides rise(s) proportionately as the amount of them present on the hair or on the skin increases, the present inventors sought to improve the binding of ceramides to and/or in the hair fiber or to and/or in the skin.

The ceramides or analogues display an insoluble character in aqueous media; hence it is necessary to employ them in a stable dispersed form. Thus, it is known to emulsify ceramides in the presence of surfactants, especially certain cationic surfactants. However, even if these emulsions prove stable, they lead to compositions whose cosmetic properties can still appear to be inadequate.

Therefore, a primary object of the invention is thus to improve the binding of ceramides to and/or in the hair fiber or to and/or in the skin.

Another object of the present invention is to provide stable aqueous dispersions based on lipid ceramide compounds.

A third object of the invention is to provide cosmetic compositions displaying improved cosmetic properties, especially with respect to the hold of the hairstyle.

The inventors have discovered that a peptide having at least one fatty chain enables these objects to be achieved.

Accordingly, the subject of the present invention is a cosmetic composition comprising, in a cosmetically acceptable aqueous medium, at least one lipid ceramide compound and at least one peptide having at least one fatty chain.

The subject of the invention is also an aqueous dispersion comprising, in an aqueous medium, at least one lipid ceramide compound and at least one peptide having at least one fatty chain.

A further subject of the invention is the use of this aqueous dispersion for preparing the aqueous composition according to the invention.

The invention also relates to the use of a peptide having at least one fatty chain as an agent for dispersing a lipid ceramide compound in an aqueous dispersion containing such compounds.

Another subject of the invention relates to a process for treating the skin or keratinous fibers such as hair.

The process comprises applying cosmetic compositions according to the invention to the skin or to keratinous fibers.

The various subjects of the invention will now be dealt with in detail. The meanings and definitions of the compounds used in the present invention, given below, are collectively valid for all of the subjects of the invention.

Lipid ceramide compound is understood to mean any lipid compound displaying properties similar to those of the ceramides, especially a barrier effect and an effect of strengthening cuticular cohesion. These compounds can possess a structure analogous to natural or synthetic unglycosylated ceramides.

Preferred lipid ceramide compounds according to the invention correspond to the formula (I):

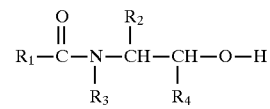

in which:

—$R_1$ denotes either a saturated or unsaturated, linear or branched $C_9$–$C_{30}$ hydrocarbon radical, it being possible for this radical to be substituted with one or more hydroxyl groups optionally esterified with a saturated or unsaturated $C_{16}$–$C_{30}$ fatty acid; or a radical R"—NR—CO—R'—, R denotes hydrogen or a mono- or polyhydroxylated, preferably monohydroxylated, $C_1$–$C_{10}$ hydrocarbon radical, R' and R" are hydrocarbon radicals in which the sum of the carbon atoms is from 9 to 30, R' being a bivalent radical, —$R_2$ denotes a hydrogen atom or a saturated or unsaturated $C_{16}$–$C_{27}$ hydrocarbon radical, it being possible for this radical to be substituted with one or more $C_1$–$C_{14}$ alkyl radicals; $R_2$ can also denote a $C_{15}$–$C_{26}$ α-hydroxyalkyl radical, the hydroxyl group being optionally esterified with a $C_{16}$–$C_{30}$ α-hydroxy acid, —$R_3$ denotes a hydrogen atom, a saturated or unsaturated $C_{16}$–$C_{27}$, hydrocarbon radical or a radical —$CH_2$—CHOH—$CH_2$—O—$R_6$ in which $R_6$ denotes a $C_{10}$–$C_{26}$ hydrocarbon radical, —$R_4$ denotes a hydrogen atom or a mono- or polyhydroxylated $C_1$–$C_4$ hydrocarbon radical.

Preferred compounds of formula (I) are the ceramides described by DOWNING (types 1 to 6 ceramides) in Arch. Dermatol, Vol. 123, 1381–1384, 1987, or those described in French Patent Application FR-2,673,179, the teachings of which are hereby incorporated by reference.

Types 1 to 6 ceramides have the following structure:

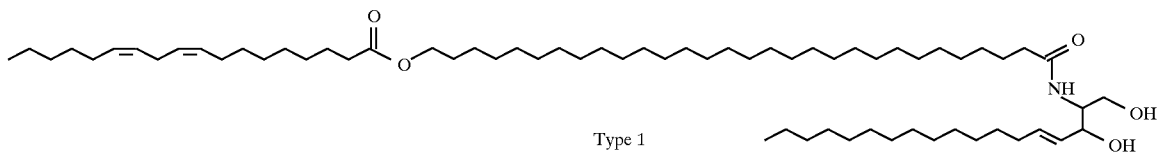

Type 1

-continued

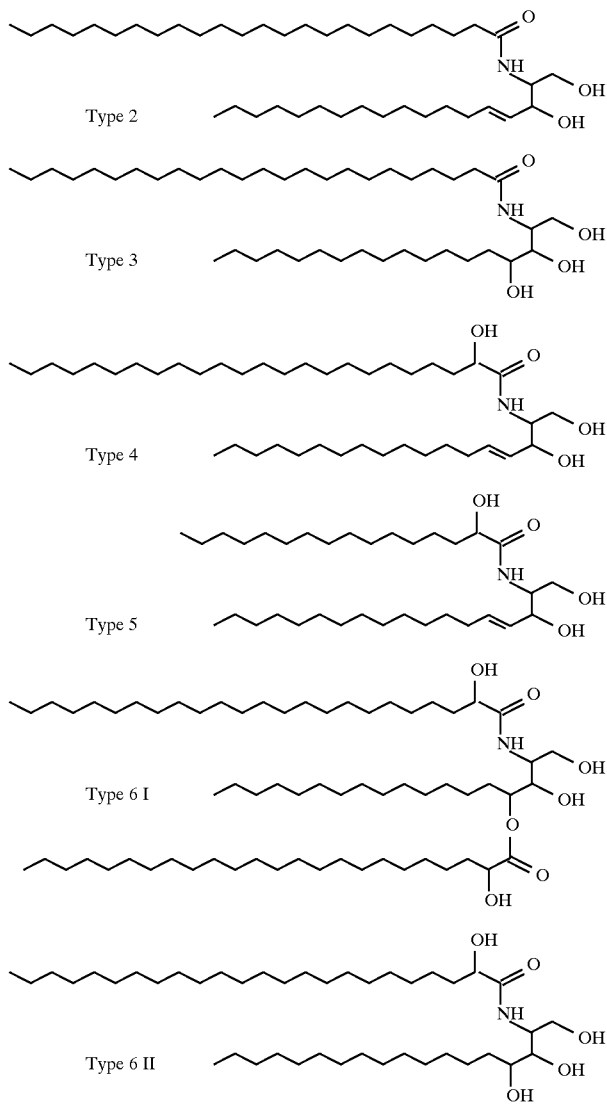

The ceramides which are most especially preferred according to the invention are the compounds of formula (I) for which $R_1$ denotes a saturated or unsaturated alkyl radical derived from $C_{16}$–$C_{22}$ fatty acids, and $R_2$ denotes a saturated linear $C_{15}$ hydrocarbon radical.

Such compounds are, for example:
N-linoleoyldihydrosphingosine,
N-oleoyldihydrosphingosine,
N-palmitoyldihydrosphingosine,
N-stearoyldihydrosphingosine,
N-behenoyldihydrosphingosine,
or mixtures of these compounds.

It is also possible to use the compounds of formula (I) described in Patent Applications EP-A-0227994 and WO 94/07844, the disclosures of which are hereby incorporated by reference. Such compounds are, for example, QUESTAMIDE H (bis(N-hydroxyethyl-N-cetyl)malonamide) sold by the company QUEST, and cetylic acid N-(2-hydroxyethyl)-N-(3-cetyloxy-2-hydroxypropyl)amide.

It is also possible to use N-docosanoyl-N-methyl-D-glucamine as described in Patent Application WO 92/05764, the disclosure of which is hereby incorporated by reference.

The concentration of lipid ceramide compounds in the cosmetic composition according to the invention preferably varies from 0.0001% to 10% by weight approximately relative to the total weight of the composition, and more preferably from 0.0001% to 5% approximately.

The subject of the present invention is also an aqueous dispersion comprising at least one lipid ceramide compound and at least one peptide having at least one fatty chain.

This aqueous dispersion has the advantage of being stable, and may hence be readily used for preparing the cosmetic composition according to the present invention.

The aqueous dispersion according to the invention preferably has a concentration of lipid ceramide compound varying from 0.0001% to 15% by weight approximately relative to the total weight of the said dispersion, and more preferably from 0.0001% to 10% approximately.

Peptide is understood to mean any compound having at least one peptide bond, such as, in particular, proteins or protein hydrolysates.

The proteins having at least one fatty chain which are usable in the present invention are either of natural origin or of synthetic origin. The protein hydrolysates having at least one fatty chain correspond to hydrolysed proteins, the fatty chain or chains coming from the hydrolysed proteins or being supplied after hydrolysis.

The fatty chain or chains of the peptides of the invention are introduced, if they are not naturally present, by chemical modification such as by grafting or by quaternization. The fatty chain or chains can comprise from 8 to 40 carbon atoms, and preferably from 10 to 22 carbon atoms. Cocoyl, lauryl or stearyl chains may, for example, be mentioned. As is well known to those skilled in the art, the fatty chain is covalently bonded to the remainder of the peptide.

The peptides having at least one fatty chain according to the invention advantageously have a molecular weight above 1000 and preferably not more than 200,000. More preferably, the molecular weight of the peptides ranges from 5,000 to 70,000.

The proteins which are usable according to the invention can be derived from matter of animal or vegetable origin. As proteins of animal origin, keratin, elastin, collagen, proteins extracted from milk, such as lactoferrin, casein, sodium, magnesium or calcium caseinate, buttermilk proteins, whey proteins including α-lactalbumin, β-lactoglobulin and immunoglobulins, and egg-white albumin, may be mentioned in particular.

As examples of proteins of vegetable origin, the proteins extracted from wheat, wheatgerm, oats, barley, maize, rice, soya, broad beans, cotton seed, lupin seed, potatoes and apricot kernels may be mentioned in particular.

In these examples, some proteins do not have a fatty chain; they then have to be modified chemically so as to have one.

In the present invention, it is preferable to use protein hydrolysates having at least one fatty chain.

Thus, as protein hydrolysates having at least one fatty chain which are especially suitable for the present invention, the following may be mentioned in particular:

- wool keratin hydrolysates bearing N-hydroxypropyl-dimethylcocoylamidopropylammonium groups such as the ones sold under the name "MONTEINE LKA" by the company SEPPIC, or cocoyldimethyl-N-hydroxypropylammonium groups such as the ones sold under the names "CROQUAT WKP" by the company CRODA, or stearyldimethyl-N-hydroxypropyl-ammonium groups such as the ones sold under the name "PROMOIS WK-HSAQ" by the company SEIWA KASEI,
- keratin hydrolysates bearing lauryldimethylammonium groups such as the ones sold under the name "CROQUAT K" by the company CRODA,
- casein hydrolysates bearing lauryldimethylammonium groups such as the ones sold under the name "HYDROLACTIN QL" by the company CRODA,
- silk fibroin hydrolysates bearing cocoyldimethyl-N-hydroxypropylammonium groups such as the ones sold under the names "PROMOIS SILK-CAQ" by the company SEIWA KASEI or "CROSILKQUAT" by the company CRODA, or lauryldimethyl-N-hydroxypropylammonium groups such as the ones sold under the name "PROMOIS SILK-LAQ" by the company SEIWA KASEI, or stearyldimethyl-N-hydroxypropylammonium groups such as the ones sold under the name "PROMOIS SILK-SAQ" by the company SEIWA KASEI,
- collagen hydrolysates bearing N-hydroxypropyl-dimethyllaurylamidopropylammonium groups such as the ones sold under the name "MONTEINE LCQ" by the company SEPPIC, or N-hydroxypropylcocoyldimethylammonium groups such as the ones sold under the name "LEXEIN QX 3000" by the company INOLEX, or stearyltrimethylammonium groups such as the ones sold under the name "QUAT-COLL QS" by the company QUIMDIS,
- wheat protein hydrolysates bearing stearyldimethyl-N-hydroxypropylammonium groups such as the ones sold under the name "HYDROTITICUM QS" by the company CRODA, or lauryldimethyl-N-hydroxypropylammonium groups such as the ones sold under the name "HYDROTITICUM QL" by the company CRODA, or cocoyldimethyl-N-hydroxypropyl-ammonium groups such as the ones sold under the name "HYDROTITICUM QM" by the company CRODA,
- soya protein hydrolysates bearing lauryldimethyl-N-hydroxypropylammonium groups such as the ones sold under the name "PROMOIS WS-LAQ" by the company SEIWA KASEI or "CROQUAT SOYA" by the company CRODA, or cocoyldimethylammonium groups such as the ones sold under the name "PROMOIS WS-CAQ" by the company SEIWA KASEI.

The concentration of peptide having at least one fatty chain in the cosmetic composition according to the invention preferably varies from 0.01% to 30% by weight approximately relative to the total weight of the composition, and more preferably from 0.1 to 10% by weight.

The aqueous dispersion according to the invention, which may be used, in particular, for preparing the cosmetic composition according to the invention, preferably has a concentration of peptides having at least one fatty chain varying from 0.01% to 40% by weight approximately relative to the total weight of the said dispersion, and preferably from 0.5 to 20% approximately.

The ratio of the concentrations by weight of peptide to lipid ceramide compound in the cosmetic composition, as well as in the aqueous dispersion, is advantageously from 1.5 to 10, and preferably from 2 to 6.

The composition according to the invention can also contain at least one additive chosen from thickeners, soluble or insoluble, volatile or non-volatile silicones, surfactants, perfumes, pearlescent agents, preservatives, sunscreen agents, proteins, vitamins, polymers, vegetable, animal, mineral or synthetic oils and any other additives traditionally used in the cosmetics field.

These additives are present in the composition according to the invention in proportions which can range from 0 to 20% by weight relative to the total weight of the composition. The precise amount of each additive is readily determined by a person skilled in the art according to its nature and its function.

The subject of the invention is also a process for treating the skin or keratinous fibers such as hair, consisting of applying a cosmetic composition as defined above to the skin or to the keratinous fibers, and in then optionally performing a rinse with water. Thus, this process according to the invention permits maintenance of the hairstyle, and treatment, care or washing of the skin, hair or any other keratinous substance.

The cosmetic compositions according to the invention can take the form of gel, milk, cream, more or less thickened lotion or mousse, and can be used for the skin or hair.

For the hair, they are, more especially, shampoos, compositions to be rinsed or otherwise, to be applied before or after shampooing, dyeing, bleaching, permanent-waving or straightening, or hair dyeing, bleaching, permanent-waving or straightening compositions. The compositions can also be hair-setting lotions, blow-drying lotions, fixing compositions (lacquers) and styling compositions. The lotions may be packaged in various forms, in particular in vaporizers or pump bottles or in aerosol cans so as to effect an application of the composition in vaporized form or in the form of a mousse. Such forms of packaging are indicated, for example, when it is desired to obtain a spray, a lacquer or a mousse for the fixing or treatment of hair.

When the composition according to the invention is packaged in aerosol form for the purpose of obtaining an aerosol lacquer or mousse, it comprises at least one propellant which may be chosen from volatile hydrocarbons such as n-butane, propane, isobutane, pentane, chlorinated and/or fluorinated hydrocarbons and mixtures thereof. It is also possible to use carbon dioxide, nitrous oxide, dimethyl ether, nitrogen or compressed air as a propellant.

The present invention also relates to a method of dispersing a lipid ceramide compound in an aqueous dispersion containing the lipid ceramide compound. the method comprises the step of including in the aqueous dispersion an effective amount of at least one peptide having at least one fatty chain.

Further, the present invention relates to a process for increasing the binding of a lipid ceramide compound to keratinous fibers or skin. This process comprises preparing a cosmetic composition containing, in an aqueous medium, at least one lipid ceramide compound and at least one peptide having at least one fatty chain, wherein the peptide is included to increase the binding of a lipid ceramide compound to keratinous fibers or skin. The process may additionally include the step of contacting the keratinous fibers or skin with the composition in the aqueous medium.

In all of what follows or of the foregoing, the percentages expressed are by weight.

The invention will now be illustrated more completely by means of the examples which follow, which could not be considered to limit it to the embodiments described. In the examples, AS denotes active substance.

EXAMPLE 1

A composition 1A having the following formulation was prepared:

| | |
|---|---|
| N-oleoyldihydrosphingosine | 0.1 g |
| Wool keratin hydrolysate quaternized with N-cocoyldimethylammonium chloride, in aqueous solution containing 30% AS (sold under the name CROQUAT WKP by the company CRODA) | 0.5 g AS |
| Water qs | 100 g |

The pH was adjusted to 5.

A composition 1B (comparative) having the following formulation was prepared:

| | |
|---|---|
| N-Oleoyldihydrosphingosine | 0.1 g |
| Quaternium-27 (REWOQUAT W75 PG from REWO) | 0.5 g AS |
| Water qs | 100 g |

The pH was adjusted to 5.

The procedure was as follows: 5 g of the above composition were applied to a lock of hair weighing 2.5 g; the composition was then left in place for 10 minutes and the lock was thereafter rinsed 3 times, passing it twice through 200 ml of water each time. The lock was then dried with a hairdryer.

To compare the amount of lipid ceramide compound bound to the hair, the same amount of composition 1B above was applied to a lock of hair of the same quality. The procedure was identical.

Each lock was divided into two and the ceramide was extracted by extraction with dichloromethane (2 times 20 ml for 1 hour at room temperature with mechanical stirring). The amides were then separated from the lipids of the hair fiber by TLC (thin-layer chromatography). The ceramide was then assayed by photodensitometry after carbonization with a solution containing 3% by weight of sulphuric acid, followed by transfer to an oven at 180° C. (a known amount of ceramide was used as reference).

The results were collated in the following table:

| | Amount of ceramide extracted per g of hair |
|---|---|
| Composition 1A (according to the invention) | 229 μg |
| Composition 1B (comparative) | 149 μg |

The amount of ceramide bound to the hair was much larger with the composition according to the invention.

The liveliness of two locks of hair weighing 2.5 g (treated with the composition 1A or 1B respectively) was also compared. Liveliness was evaluated in terms of the return of wavy hair to its initial position after a comb or brush has been passed through it.

5 g of composition were applied to a lock of hair weighing 2.5 g; the composition was left in place for 10 minutes and the lock was thereafter rinsed 3 times, passing it twice through 200 ml of water each time. The lock was then wound on curlers and thereafter dried with a hairdryer.

A panel of ten testers was then asked to say which lock was the livelier. All ten testers indicated the lock treated with the composition 1A according to the invention.

EXAMPLE 2

A hair-care mousse of the following composition was prepared:

| | |
|---|---|
| Wheat protein hydrolysate bearing an isostearyl fatty chain, in alcoholic solution containing 34% of active substance (AS), sold under the name CROTEIN ADW by the company CRODA | 0.3 g AS |
| Ceramide, type 5 | 0.1 g |
| Preservative, perfume qs | |
| HCl qs pH 8 | |
| Water qs | 100 g |
| Pressurization scheme: | |
| Above composition: | 90 g |
| Ternary mixture of n-butane, isobutane and propane (23:55:22), sold under the name "AEROGAZ 3,2 N" by the company ELF AQUITAINE | 10 g |

When applied to wet hair, this mousse melted rapidly into the hair and improved the disentangling of the wet hair. The dried hair obtained was lively and soft.

EXAMPLE 3

A hair conditioner to be rinsed of the following composition was prepared:

| | |
|---|---|
| Wool keratin hydrolysate quaternized with N-cocoyldimethylammonium chloride, in aqueous solution containing 30% of AS, sold under the name CROQUAT WKP by the company CRODA | 0.5 g AS |
| N-Oleoyldihydrosphingosine | 0.1 g |
| Vinylpyrolidone/dimethylaminoethyl methacrylate copolymer in 20% aqueous solution, sold under the name Copolymere 845 by the company ISP | 1 g AS |
| Acrylamide/ethyltrimethylammonium chloride methacrylate (52:48) crosslinked copolymer, in 50% dispersion in a mineral oil (SALCARE SC 92 from ALLIED COLLOID) | 2 g AS |
| Preservative, perfume qs | |
| NaOH qs pH 4.5 | |
| Water qs | 100 g |

When applied to wet and rinsed hair after a period of exposure, this care product improved the disentangling of the wet hair and brought smoothness and softness to dried hair.

EXAMPLE 4

A lotion of the following composition was prepared;

| | |
|---|---|
| Cetylic acid N-(2-hydroxyethyl)-N-(3-cetyloxy-2-hydroxypropyl)amide | 0.1 g |
| Wool keratin hydrolysate quaternized with N-cocoyldimethylammonium chloride, in aqueous solution containing 30% of AS, sold under the name CROQUAT WKP by the company CRODA | 0.5 g AS |
| Preservative, perfume qs | |
| Water qs natural pH 4.2 | 100 g |

This lotion was applied to wet hair. After rinsing, the hair was easy to disentangle and supple.

EXAMPLE 5

A lotion of the following composition was prepared:

| | |
|---|---|
| Bis(N-hydroxyethyl-N-cetyl)malonamide sold by Quest International under the name Questamide H | 0.1 g |
| Wool keratin hydrolysate quaternized with N-cocoyldimethylammonium chloride, in aqueous solution containing 30% of AS, sold under the name CROQUAT WKP by the company CRODA | 0.5 g AS |
| Preservative, perfume qs | |
| Water qs Natural pH 4.5 | 100 g |

When applied to washed hair, this lotion brought softness to wet hair and a smooth, coated feel to dried hair.

EXAMPLE 6

| | |
|---|---|
| Ceramide, type 2 | 10 g |
| Wool keratin hydrolysate quaternized with N-cocoyldimethylammonium chloride, in aqueous solution containing 30% of AS, sold under the name CROQUAT WKP by the company CRODA | 24 g AS |
| Preservative, perfume qs | |
| Water qs Natural pH 4 | 100 g |

This thick cream was applied to wet hair and endowed it, after rinsing, with good cosmetic properties (disentangling and softness).

What is claimed is:

1. A cosmetic composition comprising, in a cosmetically acceptable aqueous medium, at least one lipid ceramide compound and at least one peptide having at least one fatty chain, wherein said at least one lipid ceramide compound is N-linoleoyldihydrosphingosine, N-oleoyldihydrosphingosine, N-palmitoyldihydrosphingosine, N-stearoyldihydrosphingosine, N-behenoyldihydrosphingosine, bis(N-hydroxyethyl-N-cetyl)malonamide, cetylic acid N-(2-hydroxyethyl)-N-(3-cetyloxy-2-hydroxypropyl)amide, N-docosanoyl-N-methyl-D-glucamine, or mixtures thereof; and wherein said at least one peptide having at least one fatty chain is a wool keratin hydrolysate quaternized with N-cocoyldimethylammonium chloride.

2. An aqueous dispersion comprising at least one lipid ceramide compound and at least one peptide having at least one fatty chain, wherein said at least one lipid ceramide compound is N-linoleoyldihydrosphingosine, N-oleoyldihydrosphingosine, N-palmitoyldihydrosphingosine, N-stearoyldihydrosphingosine, N-behenoyldihydrosphingosine, bis(N-hydroxyethyl-N-cetyl)malonamide, cetylic acid N-(2-hydroxyethyl)-N-(3-cetyloxy-2-hydroxypropyl)amide, N-docasanoyl-N-methyl-D-glucamine, glucamine, or mixtures thereof; and wherein said at least one peptide having at least one fatty chain is a wool keratin hydrolysate quaternized with N-cocoyidimethylammonium chloride.

3. A process for dispersing a lipid ceramide compound in an aqueous dispersion containing said compound, comprising the step of including in said dispersion an effective amount of at least one peptide having at least one fatty chain, wherein said at least one lipid ceramide compound is N-linoleoyldihydrosphingosine, N-oleoyldihydrosphingosine, N-palmitoyldihydrosphingosine, N-stearoyldihydrosphingosine, N-behenoyldihydrosphingosine, bis(N-hydroxyethyl-N-cetyl)malonamide, cetylic acid N-(2-hydroxyethyl)-N-(3-cetyloxy-2-hydroxypropyl)amide, N-docosanoyl-N-methyl-D-glucamine, or mixtures thereof; and wherein said at least one peptide having at least one fatty chain is a wool keratin hydrolysate quaternized with N-cocoyldimethylammonium chloride.

4. A process for increasing the binding of a lipid ceramide compound to keratinous fibers of skin comprising the step of:

preparing a cosmetic composition containing, in an aqueous medium, at least one lipid ceramide compound and at least one peptide having at least one fatty chain, wherein said peptide is included to increase said binding of a lipid ceramide compound to keratinous fibers of skin, wherein said at least one lipid ceramide compound is N-linoleoyldihydrosphingosine, N-oleoyldihydrosphingosine, N-palmitoyldihydrosphingosine, N-stearoyldihydrosphingosine, N-behenoyldihydrosphingosine, bis(N-hydroxyethyl-N-cetyl)malonamide, cetylic acid N-(2-hydroxyethyl)-N-(3-cetyloxy-2-hydroxypropyl)amide, N-docosanoyl-N-methyl-D-glucamine, or mixtures thereof; and wherein said at least one peptide having at least one fatty chain is a wool keratin hydrolysate quaternized with N-cocoyldimethylammonium chloride.

5. The composition according to claim 1, wherein said at least one lipid ceramide compound is present in concentrations ranging from 0.0001 to 10% by weight relative to the total weight of the composition.

6. The composition according to claim 5, wherein said at least one lipid ceramide compound is present in concentrations ranging from 0.0001 to 5% by weight relative to the total weight of the composition.

7. The composition according to claim 1, wherein the concentration of said at least one peptide ranges from 0.01 to 30% by weight relative to the whole composition.

8. The composition according to claim 7, wherein the concentration of said at least one peptide ranges from 0.1 to 10% by weight relative to the whole composition.

9. The composition according to claim 1, wherein the ratio of the concentrations by weight of said at least one peptide to said at least one lipid ceramide compound ranges from 1.5 to 10.

10. The composition according to claim 9, wherein the ratio of the concentrations by weight of said at least one peptide to said at least one lipid ceramide compound ranges from 2 to 6.

11. The aqueous dispersion according to claim 2, wherein the concentration of said at least one lipid ceramide compound varies from 0.0001 to 15% by weight relative to the total weight of said dispersion.

12. The aqueous dispersion according to claim 11, wherein the concentration of said at least one lipid ceramide compound varies from 0.0001 to 10% by weight relative to the total weight of said dispersion.

13. The aqueous dispersion according to claim 2, wherein the concentration of said at least one peptide ranges from 0.01 to 40% by weight relative to the total weight of said dispersion.

14. The aqueous dispersion according to claim 13, wherein the concentration of said at least one peptide ranges from 0.5 to 20% by weight relative to the total weight of said dispersion.

15. The aqueous dispersion according to claim 2, wherein the ratio of the concentrations by weight of said at least one peptide to said at least one lipid ceramide compound ranges from 1.5 to 10.

16. The aqueous dispersion according to claim 15, wherein the ratio of the concentrations by weight of said at least one peptide to said at least one lipid ceramide compound ranges from 2 to 6.

17. A process for treating skin comprising the step of applying to the skin a cosmetic composition according to claim 1.

18. A process for treating keratinous fibers comprising the step of applying to said keratinous fibers a cosmetic composition according to claim 1.

19. The process of claim 18, wherein said keratinous fibers are hair.

* * * * *